United States Patent [19]

Riediker et al.

[11] Patent Number: 4,855,468

[45] Date of Patent: Aug. 8, 1989

[54] TITANOCENES AND A RADIATION-POLYMERIZABLE COMPOSITION CONTAINING THESE TITANOCENES

[75] Inventors: Martin Riediker, Riehen; Kurt Meier, Allschwil; Hans Zweifel, Basel, all of Switzerland

[73] Assignee: Ciba-Geigy Corporation, Ardsley, N.Y.

[21] Appl. No.: 99,362

[22] Filed: Sep. 11, 1987

Related U.S. Application Data

[62] Division of Ser. No. 807,565, Dec. 11, 1985, Pat. No. 4,713,401.

[30] Foreign Application Priority Data

Dec. 20, 1984 [CH] Switzerland .......................... 6051/84

[51] Int. Cl.$^4$ ................................................ C07F 7/28
[52] U.S. Cl. ....................................... 556/53; 544/64; 544/225; 546/4; 548/103; 549/3; 556/11; 556/28; 556/31; 522/12; 204/159.13; 204/159.24; 430/286; 552/4
[58] Field of Search .................. 556/11, 28, 31; 546/2, 546/4; 548/101, 103; 544/64, 225; 549/3

[56] References Cited

U.S. PATENT DOCUMENTS

4,548,891 10/1985 Riediker et al. .................... 430/283
4,590,287  5/1986 Riediker et al. ...................... 556/53

OTHER PUBLICATIONS

"Hackh's Chemical Dictionary," pp. 35–36 (1969).

*Primary Examiner*—Michael L. Shippen
*Attorney, Agent, or Firm*—Luther A. R. Hall; JoAnn Villamizar

[57] ABSTRACT

Titanocenes with $\pi$-cyclopentadienyl ligands, in which one or two carbocyclic or heterocyclic aromatic rings are bonded to the metal, the aromatic rings being substituted in at least one of the two ortho-positions relative to the metal-carbon bonds by $CF_2Z$ (Z=F or substituted or unsubstituted alkyl), are suitable as photoinitiators for the photopolymerization of ethylenically unsaturated compounds. They are distinguished by a high radiation sensitivity, stability to air and thermal effects, and high effectiveness in the range from UV light to visible light.

8 Claims, No Drawings

TITANOCENES AND A RADIATION-POLYMERIZABLE COMPOSITION CONTAINING THESE TITANOCENES

This is a divisional of application Ser. No. 807,565, filed on Dec. 11, 1985, now U.S. Pat. No. 4,713,401, issued on Dec. 15, 1987.

The present invention relates to metallocenes with at least one aromatic radical containing a fluoroalkyl group, to a photopolymerizable composition which consists of ethylenically unsaturated compounds and contains these metallocenes as photoinitiators, to a substrate coated with this composition and to a process for producing photographic relief images by using this coated substrate.

In EP-A No. 0,122,223, titanocenes with fluorine-substituted aromatic radicals are described, which are suitable as photoinitiators for the polymerization of ethylenically unsaturated compounds. The titanocenes are substituted in the aromatic radical by at least one fluorine atom in the Ortho-position relative to the metal-carbon bond and, to be effective and thermally stable, they must contain two such radicals.

The present invention relates to titanocenes of the formula I

in which the two $R^1$ independently of one another are unsubstituted or substituted cyclopentadienyl$^\ominus$, idenyl$^\ominus$, 4,5,6,7-tetrahydroindenyl$^\ominus$ or both $R^1$ together are an unsubstituted or substituted radical of the formula II

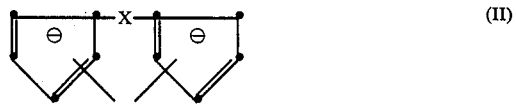

in which X is $-(CH_2)_n-$ with n=1, 2 or 3, alkylidene having 2 to 12 C atoms, cycloalkylidene having 5 to 7 ring carbon atoms, $SiR_2^4$ or $SnR_2^4$ and $R^4$ is $C_1$-$C_{12}$-alkyl, $C_5$-$C_{12}$-cycloalkyl, $C_6$-$C_{16}$-aryl or $C_7$-$C_{16}$-aralkyl, $R_2$ is a 6-membered carbocyclic or 5-membered or 6-membered heterocyclic aromatic ring which is substituted in at least one of the two ortho-positions relative to the metal-carbon bond by $-CF_2Z$, in which Z is F or unsubstituted or substituted alkyl, it being possible for the aromatic ring to contain further substituents, and $R^3$ is as defined for $R^2$ or is halogen pseudohalogen, $-OH$, alkoxy, alkylthio, aryloxy, arylthio, acyloxy, secondary amino, alkynyl, phenylalynyl, substituted aryl, $-Si_3^4$ or $-SnR_3^4$ $R^4$ being as defined above.

The groups $R^1$ preferably are identical radicals. The substituents for $R^1$ can be: Linear or branched alkyl, alkoxy and alkenyl preferably having 1 to 18, in particular 1 to 12 and especially 1 to 6 carbon atoms, such as methyl, ethyl, propyl, isopropyl, n-butyl, tert.-butyl, pentyl, hexyl, octyl, decyl, dodecyl, tetradecyl, hexadecyl, octadecyl and corresponding alkenyl and alkoxy groups; cycloalkyl and cycloalkeyl having preferably 5 to 8 ring carbon atoms, for example cyclopentyl, cyclohexyl, cycloheptyl, methylcyclopentyl and methylcyclohexyl; aryl having preferably 6 to 16 C atoms and aralkyl having preferably 7 to 16 C atoms, for example phenyl, naphthyl, pyridinyl, benzyl and phenylethyl; cyano, halogen, in particular F, Cl and Br, and amino, in particular tertiary amino which can contain linear or branched alkyl groups having 1 to 12, especially 1 to 6, C atoms and in particular methyl and ethyl, phenyl and benzyl. The amino groups can also be quaternized, in particular with linear or branched alkyl halides having preferably 1 to 12 C atoms, in particular methyl or ethyl halides; linear or branched aminoalkyl, in particular tertiary aminoalkyl which can also be quaternized, in particular with alkyl halides. The alkylene group in the aminoalkyl can be linear or branched and contains preferably 1 to 12, in particular 1 to 6 C atoms and most preferably in methylene which can be substituted by $C_1$-$C_{12}$-alkyl.

The radicals $R^1$ can contain up to 3 substituents but especially 1 substituent. In particular, both $R^1$ are cyclopentadienyl$^\ominus$ or $C_1$-$C_4$-alkylcyclopentadienyl$^\ominus$, especially methylcyclopentadienyl$^\ominus$.

Alkylidene X in the formula II preferably contains 2 to 6 C atoms. Examples of alkylidene and cycloalkylidene are ethylidene, propylidene, butylidene, hexylidene, phenylmethylene, diphenylmethylene, cyclopentylidene and cyclohexylidene. Alkyl $R^4$ in the group X preferably contains 1 to 6 C atoms and is, for example, methyl, ethyl, propyl, butyl or hexyl, cycloalkyl $R^4$ is preferably cyclopentyl or cyclohexyl, aryl $R^4$ is preferably phenyl and aralkyl $R^4$ is preferably benzyl. Particularly preferably, X is methylene.

The aromatic radical is substituted preferably by only one $-CF_2Z-$ group, in particular if $R^3$ and $R^2$ are identical. An alkyl Z contains preferably 1 to 12, in particular 1 to 6 C atoms. The alkyl can be partially or fully substituted especially by halogen, preferably chlorine and in particular fluorine. Particularly preferably, the $-CF_2Z-$ group is perfluoroalkyl having preferably up to 4 C atoms, and especially is a $CF_3$ group.

A 6-membered carbocyclic aromatic and $CF_2Z$-substituted ring $R^2$ can be indene, indane, fluorene, naphthalene and in particular phenyl. Examples are: 4-(trifluoromethyl)inden-5-yl, 5,7-di-(trifluoromethyl)-indan-6-yl, 2-trifluoromethyl)-fluoren-3-yl, 3-(trifluoromethyl)-naphth-2-yl and especially 2-(trifluoromethyl)-phen-1-yl.

Heterocyclic aromatic and 5-membered ring $R^2$ contains preferably one hetero atom and a 6-membered $R^2$ contains preferably 1 or 2 hetero atoms. Examples of such $-CF_2Z-$ substituted rings are: 2-(trifluoromethyl)-pyrr-3-yl, 2-(trifluoromethyl)-fur-3-yl, 2-(trifluoromethyl)-thiophen-3-yl, 2-(trifluoromethyl)-pyrid-3-yl, 3-(trifluoromethyl)-pyrid-4-yl and 4-(trifluoromethyl)-pyrimid-5-yl.

The radicals $R^2$ can be partially or fully substituted by further groups. Suitable groups are: linear or branched alkyl or alkoxy having preferably 1 to 18, in particular 1 to 6 C atoms, for example methyl, ethyl, propyl, butyl, pentyl, hexyl and the corresponding alkoxy groups, in particular methyl and methoxy; cycloalkyl having preferably 5 or 6 ring carbon atoms, aryl having preferably 6 to 16 C atoms and aralkyl having preferably 7 to 16 C atoms, for example cyclopentyl, cyclohexyl, phenyl or benzyl; hydroxyl, carboxyl, CN, halogen such as F, Cl or Br, and amino, in particular tertiary amino which can be quaternized with alkyl halides such as methyl chloride, bromide or iodide. Examples of amino are methylamino, ethylamino, dimethylamino, diethylamino, pyrrolidyl, piperidyl, piperazyl, morpholyl and N-methylpiperazyl; alkoxycarbonyl having preferably 1 to 18, in particular 1 to 6 C atoms in the alkoxy group, aminocarbonyl wherein the amino group is substituted with one or two alkyl groups having 1 to 12 C atoms; or aminocarbonyl with heterocyclic amines such as pyrrolidine, piperidine, piperazine, N-methylpiperazine and morpholine; aminoalkyl, in particular tertiary aminoalkyl which has preferably $C_1$–$C_6$-alkyl groups and can be quaternized with alkyl halides. Tertiary-aminomethyl which can be substituted by alkyl having 1 to 12 C atoms is prefered. Examples are dimethylaminomethyl and trimethylammonium-methyl iodide.

Examples of substitutents for phenylalkynyl, aryl, aryloxy and arylthio $R^3$ are halogen, such as F, Cl and Br, secondary amino, alkyl and alkoxy having 1 to 6 C atoms, carboxyl, —OH and —CN.

A halogen $R^3$ can be iodine and in particular bromine, chlorine and fluorine. A pseudohalide $R^3$ is preferably cyanate, thiocyanate, azide or cyanide.

Alkoxy and alkylthio $R^3$ can be linear or branched and can contain 1 to 12, in particular 1 to 6 C atoms. Methoxy, ethoxy, methylthio and ethylthio are preferred.

Aryloxy or arylthio $R^3$ is preferably unsubstituted or substituted phenoxy or phenylthio respectively.

Acyloxy $R^3$ is preferably the radical of an aliphatic, cycloaliphatic, aromatic, preferably monobasic carboxylic acid which can contain 1 to 18 and especially 1 to 12 C atoms. Examples of such acids are formic acid, acetic acid, monochloroacetic acid, trichloroacetic acid, trifluoroacetic acid, propionic acid, butyric acid, acrylic acid, methacrylic acid, benzoic acid, chlorobenzoic acid and phenylacetic acid.

Secondary amino $R^3$ is preferably of the formula $R^{10}R^{11}N$—, in which $R^{10}$ and $R^{11}$ are, for example, $C_1$–$C_{12}$ alkyl, unsubstituted or alkyl-substituted cyclopentyl, cyclohexyl, phenyl or benzyl, or $R^{10}$ and $R^{11}$ together are tetra-, penta- or hexa-methylene which are unsubstituted or alkyl-substituted and/or may be interrupted by —S—, —O— or —N—alkyl—. The alkyl contains preferably 1–4 C atoms. Examples are methyl, ethyl, n-propyl, n-butyl, i-butyl, t-butyl, pentyl, hexyl, methylcyclohexyl, methylphenyl, methylbenzyl, —(CH$_2$)$_2$—X'—(CH$_2$)$_2$— with X' being a direct bond, —CH$_2$—, —O—, —S— and —N—alkyl—, in which the alkyl can have 1 to 4 C atoms.

Alkynyl $R^3$ is preferably of the formula $C_xH_{2x+1}$—C≡C—, in which x is 0 or a number from 1 to 12. Examples are ethynyl, propargyl, butynyl, pentynyl and hexynyl.

Examples of substituted phenylalkynyl $R^3$ are methylphenyl-alkynyl, fluorophenyl-alkynyl and chlorophenyl-alkynyl.

Substituted aryl $R^3$ is preferably substituted phenyl and especially a radical of the formula

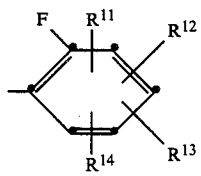

in which $R^{11}$ to $R^{14}$ are hydrogen atoms, fluorine, chlorine, bromine, $C_1$–$C_4$-alkyl, Secondary amino having 2 to 12 C atoms or tertiary amino-methyl having 3 to 18 C atoms, and the two amino groups can also be quarernized, in particular with $C_1$–$C_6$-alkyl halides, for example alkyl iodides. Preferably, only one amino group is present and is bonded in the para-position relative to the free bond. 2,6-Difluorophen-1-yl radicals, in particular pentfluorophenyl, are particularly preferred.

The radical $R^4$ is preferably $C_1$–$C_4$-alkyl, phenyl or benzyl. In particular, $R^4$ is methyl or phenyl.

In a preferred embodiment, $R^3$ is as defined for R2, and in another preferred embodiment $R^3$ is halogen or pseudohalogen.

In a preferred sub-group, $R^2$ is of the formula III

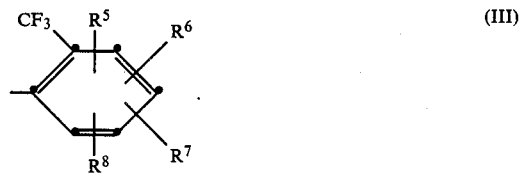

In the formula III, $R^5$, $R^6$ and $R^7$ are especially hydrogen atoms, and $R^8$ is a hydrogen atom or fluorine bonded in the ortho-position relative to the free bond.

In a particularly preferred sub-group, $R^1$ in the formula I is cyclopentadienyl$^\ominus$ or methylcyclopentadienyl$^{63}$, $R^2$ is

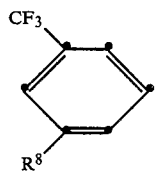

in which $R^8$ is H or F, and $R^3$ is as defined above and especially is halogen or pseudohalogen, in particular F, Cl, Br, $N_3$, CN, NCO or NCS.

The titanocenes of the formula I are prepared by known or analogous processes. The procedure can, for example, be such that a titanocene dihalide of the formula IV

wherein Y is halogen, is reacted with 2 mol of $LiR^2$ for the preparation of the titanocenes of the formula Ia

or with 1 mol of $LiR^2$ for the preparation of the titanocenes of the formula Ib

or, for the prepration of titanocenes of the formula Ic

in which $R^9$ is pseudohalogen, —OH, alkoxy, alkylthio, aryloxy, arylthio, acyloxy, secondary amino, alkynyl, phenylalkynyl, substituted aryl, $SiR_34$ or $SnR_34$, a titanocene of the formula Ib is reacted with an alkali metal compound of the formula $R^9Q$, in which Q is Li, Na or K, and the titanocenes of the formulae Ia, Ib and Ic are isolated in a manner known per se.

The known processes are described, for example, in J. Organometal. Chem., 2 (1964), pages 206–212, and J. Organometal. Chem. 4 (1965), pages 446–455.

The starting compounds of the formula IV, in which Y especially is chlorine, are known. The lithium compounds $LiR^2$ and $LiR^3$ are likewise known or can be prepared, for example by analogous processes, by reacting $R^2$-halides or $R^3$-halides, in particulr the bromides, with butyllithium.

The preparation of the titanocenes of the formula I is in general carried out in the presence of inert solvents, for example hydrocarbons or ethers, at temperatures below $-30°$ C., for example $-30°$ to $-100°$ C., preferably $-60°$ to $-90°$ C., and under inert gas blanketing. In one embodiment of the process, $LiR^2$ or $LiR^3$ is first prepared by reacting the corresponding halides in either as the solvent with lithium butyl at temperatures of about $-78°$ C. The corresponding titanocene dihalide is then added to the cooled reaction mixture, the cooling is removed and the mixture is allowed to warm to room temperature. If appropriate after the addition of solvents, the reaction mixture is then filtered and the titanocene according to the invention is isolated from solution by precipitation or by evaporation of the solvent.

The products are in general solid, crystalline and in most cases coloured compounds which are distinguished by high thermal stability and do not decompose until their melting range is approached. No decomposition is observed either under the action of air or under the action of water.

The compounds are stable on storage and can be handled without a blanketing gas. They are outstandingly suitable, even by themselves, as effective photoinitiators for the light-induced polymerization of ethylenically unsaturated compounds. In this case, they are distinguished by a high light-sensitivity and activity over a wide wavelength range from about 200 nm (UV light) up to about 600 nm. The light-sensitivity is based on the particular structure of the radical $R^2$. By contrast, similar titanocenes, in which $R^2$ is an unsubstituted or substituted phenyl radical, do not show light-sensitivity. The radical $R^3$ can be varied widely. Thus, tailor-made photoinitiators can be prepared for diverse applications. Furthermore, the spectral sensitivity (colour, absorption coefficients) and the solubility can be modified.

The present invention also relates to a composition which is polymerizable by radiation and contains (a) at least one non-volatile, monomeric, oligomeric or polymeric compound having at least one polymerizable ethylenically unsaturated double bond and (b) at least one titanocene of the formula I as a photoinitiator.

The added quantity of the metallocenes according to the invention depends essentially on economic aspects, on their solubilities and on their desired sensitivity. In general, 0.01 to 25, preferably 0.1 to 20 and especially 1 to 10% by weight are used, relative to the component (a) and a binder (c) which may be present.

Those ethyleically unsaturated monomeric, oligomeric and polymeric compounds can be used as the component (a) which react by photopolymerization to give high-molecular products and thus change their solubility.

Examples of particularly suitable compounds are esters and amides of ethylenically unsaturated carboxylic acids and polyols or polyepoxides, and polymers with ethylenically unsaturated groups in the chain or in side groups, for example unsaturated polyesters, polyamides and polyurethanes, and copolymers thereof, polybutadiene and polybutadiene copolymers, polyisoprene and polyisoprene copolymers, polymers and copolymers with (meth)acrylic groups and N-maleimidylalkyl groups in side chains, addition products of meth-/acrylic acids with diepoxides or polyepoxides, and mixtures of one or more such polymers.

Examples of unsaturated carboxylic acids are acrylic acids, methacrylic acid, crotonic acid, itaconic acid, cinnamic acid and unsaturated fatty acids such as linolenic acid or oleic acid. Acrylic and methacrylic acid are preferred.

Suitable polyols are aromatic and especially aliphatic and cycloaliphatic polyols. Examples of aromatic polyols are hydroquinone, 4,4'-dihydroxyphenylene, bisphenols such as bisphenol A, and novolaks and resols. Examples of polyepoxides are those based on the above polyols, in particular the aromatic polyols, and epichlorohydrin. Polymers or copolymers with hyrdoxyl groups in the polymer chain or in side groups, for example polyvinyl alcohol and copolymers or poly-(hydroxyalkyl methacrylates) or copolymers, are also suitable as the alcohol. Further suitable alcohols are oligoesters with terminal hydroxyl groups.

A preferred group of polyols are those of the formula $R^{15}(OH)_n$, in which $R^{15}$ is an n-valent, preferably 2- to 8-valent, in particular 2- to 6-valent aliphatic radical having 2 to 30 C atoms, which can be interrupted by nitrogen, sulfur and especially oxygen atoms and by cycloalkylene, or is cycloalkylene having 5 or 6 ring carbon atoms.

Examples of polyols are alkylene diols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols with moleculr weights of preferably 100 to 1,500, 1,3-cyclopentanediol, 1,2-, 1,3- or 1,4-cyclohexanediol, 1,4-dihydroxymethylcyclohexane, glycerol, tris-($\beta$-hydroxyethyl)-amine, trimethylolethane, trimethylolpropane, pentaerythritol, dipentaerythritol and sorbitol.

The polyols can be partially or fully esterified with one or different unsaturated carboxylic acids, and in partial esters the free hydroxyl groups can be modified, for example esterified with other carboxylic acids or etherified.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, sorbitol tetramethacrylate, sorbitol pentaacrylate, sobitol hexaacrylate, a modified pentaerythritol triacrylate, an oligoester acrylate, an oligoester methacrylate, glycerol diacrylate and triacrylate, 1,4-cyclohexane diacrylate, bis-acrylates and bis-methacrylates of polyethylene glycol of molecular weight from 100 to 1,500, or mixtures thereof.

The amides of identical or different unsaturated carboxylic acids and aromatic, cycloaliphatic and aliphatic polyamines having preferably 2 to 6, especially 2 to 4 amine groups and 2 to 30, especially 2 to 18 C atoms are also suitable as the component (a). Examples of amines are alkylenediamines having preferably 2 to 22 C atoms, such as ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-$\beta$-aminoethyl ether, diethylenetriamine, triethylenetetramine and di-($\beta$-aminopropoxy)-ethane. Polymers and copolymers with amino groups in the side chain and oligoamides with amino end groups are further suitable polyamines.

Examples are: methylene-bis-acrylamide, 1,6-hexamethylene-bis-acrylamide, diethylenetriamine-trismethacrylamide, bis-(methacrylamidopropoxy)-ethane, $\beta$-methacrylamidoethyl methacrylate and N-[($\beta$-hydroxyethoxy)-ethyl]-acrylamide.

Suitable unsaturated polyesters and polyamides are derived, for example, from maleic acid and diols or diamines. The maleic acid can be partially replaced by other dicarboxylic acids. These compounds can be employed together with ethylenically unsaturated comonomers, for example styrene. The polyesters and polyamides can also be derived from saturated dicarboxylic acids and ethylenically unsaturated diols and diamines, in particular those with longer chains having, for example 6 to 20 C atoms. Examples of polyurethanes are those which are composed of saturated or unsaturated diisocyanates and unsaturated or saturated diols.

Polybutadiene and polyisoprene, and copolymers thereof, are known. Examples of suitable comonomers are polyolefins such as ethylene, propene, butene, hexene, (meth)acrylates, acrylonitrile, styrene or vinyl chloride. Polymers with (meth)acrylate groups in the side chain are also known. These can be, for example, reaction products of epoxide resins based on bisphenol A or novolak with (meth)acrylic acid, homopolymers of copolymers of polyvinyl alcohol or hydroxyalkyl derivatives thereof which are esterified with (meth)acrylic acid, or homopolymers and copolymers of (meth)acrylates which are esterified with hydroxyalkyl (meth)acrylates.

The photopolymerizable compounds can be employed by themselves or in any desired mixtures. It is advantageous to admix esters of unsaturated carboxylic acids, in particular (meth)acrylates of polyols. In another embodiment, (meth)acrylates of polyols are used by themselves or as mixtures.

Binders (c) can also be added to the compositions according to the invention; this is particularly advantageous when the photopolymerizable compounds are liquid or viscous substances. The quantity of the binder (c) can, for example, be 5–95, preferably 10–90 and especially 50–90% by weight, relative to the quantity present of component (b) and binder (c).

The binder is selected in accordance with the field of application and the properties required for the latter, such as the ability to be developed in aqueous and organic solvent systems, adhesion to substrates and oxygen susceptibility.

Examples of suitable binders are polymers having a molecular weight of about 5,000–2,000,000, preferably 10,000 to 1,000,000. Examples are: homopolymeric and copolymeric acrylates and methacrylates, for example methyl methacrylate/ethyl acrylate/methacrylic acid copolymers poly(alkyl methacrylates), poly(alkyl acrylates), with alkyl=$C_1$–$C_{20}$-alkyl cellulose esters and ethers, such as cellulose acetate, cellulose acetate-butyrate, methylcellulose and ethylcellulose, polyvinyl butyral, polyvinyl formal, cyclized rubber, polyethers such as polyethylene oxide, polypropylene oxide and polytetrahydrofuran; polycarbonate, polyurethane, chlorinated polyolefins, polyvinyl chloride, vinyl chloride/vinylidene chloride copolymers, copolymers of vinylidene chloride with acrylonitrile, methyl methacrylate and vinyl acetate, polyvinyl acetate, copoly(ethylene/vinyl acetate), polyamides and polycaprolactams such as polycaprolactam and poly(hexamethyleneadipamide), polyesters such as poly(ethylene glycol terephthalate) and poly(hexamethylene glycol succinate).

The composition according to the invention can contain further conventional additives, for example thermal polymerization inhibitors, pigments, dyes, fillers, adhesion promoters, wetting agents and plasticizers. The compositions can also be dissolved for application in suitable solvents.

The light-sensitivity of the composition according to the invention can be further increased by the addition of sensitizers. The quantity can correspond to the quantity of the compounds of the formula I. Examples of suitable sensitizers are monocyclic or polycyclic aromatic hydrocarbons or hetero-aromatics, phenones, especially acetophenones or benzophenones, benzils, stilbenes, polyacetylenes, xanthones and thioxanthones, anthracenes, phthalimides, especially phthalimide thioether and diones with adjacent CO groups. Further examples are described in S. L. Murov, Handbook of Photochemistry, M. Dekker Inc., N.Y., pages 27 et seq. (1973). Substituted thioxanthones are preferred.

The compositions according to the invention are outstandinly suitable as coating agents for substrates of any type, for example wood, paper, ceramics, plastics such as polyester and cellulose acetate films, and metals such as copper and aluminium, to which a protective layer or a photographic image is to be applied by photopolymerization. The present invention also relates to the substrates described and to a process for applying photographic images to the substrates.

The coated substrates can be produced, for example, by preparing a solution or suspension of the composition. The choice of solvent and the concentration depend mainly on the type of the composition and on the coating process. The Solution or suspension is applied uniformly to a substrate by means of known coating processes, for example by dipping, blade coating, curtain-coating processes, brushing, spraying and reverse-roll coating. The amount applied (layer thickness) and the nature of the substrate (Carrier) depend on the desired field of application. Films of polyester of cellulose acetate or plastic-coated papers, for example, are used for the photographic recording of information; specially treated aluminium is used for offset printing formes, and copper-clad laminates for the production of printed circuits. The layer thicknesses for photographic materials and offset printing formes are about 0.5 to about 10 μm, and 1 to about 100 μm for printed circuits.

As is known, the photopolymerization of (meth)acrylates is inhibited by atmospheric oxygen, in particular in thin layers. This effect can be mitigated by known conventional methods, for example application of a polyvinyl alcohol covering layer or pre-exposure or pre-conditioning under an inert gas. Compounds suppressing the action of oxygen can also be added. Such compounds are described in U.S. Pat. Nos. 3,479,185 and 4,414,312.

After coating, the solvent is removed by drying, and this gives a layer of the light-sensitive polymer on the carrier. After the imagewise exposure of the material through a photomask, carried out in the conventional manner, the unexposed areas of the polymer are removed by dissolving them out in a developer and the polymer relief, consisting of crosslinked polymer according to the invention, is bared. The type of developer can be of aqueous or organic nature, depending on the type and composition of the photopolymerizable layer. For example, aqueous carbonate solutions are suitable for compounds containing carboxyl groups and for binders. Examples of suitable organic binders are chlorinated hydrocarbons such as 1,1,1-trichloroethane, ketones such as cyclohexanone, esters such as butyl acetate and acetoxymethoxyethane, and alcohols such as ethylcellosolve, methylcellosolve and butanol.

The light-sensitivity of the materials according to the invention extends from the UV region (200 nm) up to about 600 nm and thus covers a very wide range. A large number of very diverse types of light sources can therefore be used. Both point sources and large-area emitters (lamp arrays) are suitable. Examples are: carbon arc lamps, xenon arc lamps, mercury vapour lamps, if appropriate doped with metal halides (metal halide lamps), fluorescence lamps, incadescent argon lamps, electronic flash lamps and photographic floodlights. The distance between the lamp and the image material according to the inventon can vary, for example between 2 cm and 150 cm, depending on the particular application and on the type and intensity of the lamp. Laser light sources, for example argon ion lasers or krypton ion lasers with intense emission lines (Ar laser) at 457, 476, 488, 514 and 528 nm, are especially suitable. In this type of exposure, a photomask in contact with the photopolymer layer is no longer necessary; the controlled laser beam writes directly on the layer. In this case, the high sensitivity of the materials according to the invention is very advantageous; it allows high writing speeds at relatively low intensities. Printed circuits in the electronics industry, lithographic offset printing plates or relief printing plates as well as photographic image-recording materials can be produced by this method.

The most important applications are the use as an etch resist, plating resist and solder resist in the production of printed circuits and printing plates, the production of photopolymer printing plates for offset printing, letterpress printing (relief printing) and in flexographic printing and screen printing as a staging ink, and for the production of photographic image-recording materials, for example according to DE-A No. 2,651,864 or DE-A No. 2,202,360.

The examples which follow illustrate the invention in more detail.

EXAMPLES 1-11

50 ml of butyllithium (1.6-molar solution in hexane=80 mmol) and 150 ml of diethyl ether are placed into a 500 ml three-necked round-bottomed flask under argon and cooled to −70° C. 16.9 g of o-bromo-trifluoromethylbenzene (=75 mmol) in 150 ml of diethyl ether are then added dropwise within 1 hour and stirring of the mixture is continued for 1 hour at −70° C. 17.5 g of $Cp_2TiCl_2$ (=70.5 mmol) are are added and the reaction mixture is slowly warmed within 3 hours up to room temperature, while excluding light, an orange suspension being formed. For working up, the mixture is evaporated to dryness in a rotary evaporator, and the highly viscous residue is taken up in 150 ml of $CH_2Cl_2$, filtered over Hyflo and again evaporated. For precipitating the product, the residue is stirred up with 300 ml of n-hexane. This gives 22.2 g of an orange crystalline product (=88% of theory).

An analogous procedure is followed in Examples 2–8. The reaction conditions and results are given in Tables 1 and 2. Cp symbolises cyclopentadienyl$^\ominus$.

EXAMPLES 12-20

9.7 g (0.025 mol) of the product from Example 3 and 5.5 g of potassium thiocyanate in 125 ml of acetone are stirred in a 250 ml round-bottomed flask for 18 hours at room temperature, while excluding light. The salt which has precipitated is then filtered off, the solvent is evaporated (rotary evaporator) and the dark-red residue is crystallized from 100 ml of n-hexane. This gives 7.3 g (=71%) of crystalline product.

An analogous procedure is followed in Examples 13–20. The reaction conditions and results are given in Tables 1 and 2.

TABLE 1

| | | Starting material/reaction conditions | | | |
|---|---|---|---|---|---|
| Example | Ti compound | Lithium butyl in hexane (1.6 M) | Fluoroaromatic | Solvent | Temperature |
| 1 | 17.5 g $Cp_2TiCl_2$ | 50 ml | 16.9 g 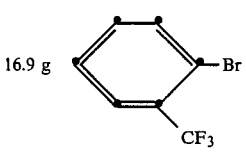 | 300 ml ether | −70° C. |

TABLE 1-continued

| | Starting material/reaction conditions | | | | |
|---|---|---|---|---|---|
| 2 | 18.5 g Cp$_2$TiCl$_2$ | 100 ml | 35 g of 1-bromo-2-(trifluoromethyl)benzene (dimetallated at 3,4-positions) | 500 ml ether | −70° C. |
| 3 | 78 g (CH$_3$Cp)$_2$TiCl$_2$ | 200 ml | 67.6 g of 1-bromo-2-(trifluoromethyl)benzene (dimetallated at 3,4-positions) | 800 ml ether | −70° C. |
| 4 | 20.6 g Cp$_2$TiBr$_2$ | 50 ml | 16.9 g of 1-bromo-2-(trifluoromethyl)benzene (dimetallated at 3,4-positions) | 250 ml ether | −70° C. |
| 5 | 25.7 g (CH$_3$Cp)$_2$TiBr$_2$ | 50 ml | 16.9 g of 1-bromo-2-(trifluoromethyl)benzene (dimetallated at 3,4-positions) | 250 ml ether | −70° C. |
| 6 | 15.2 g Cp$_2$TiF$_2$ | 50 ml | 16.9 g of 1-bromo-2-(trifluoromethyl)benzene (dimetallated at 3,4-positions) | 250 ml ether | −70° C. |
| 7 | 17 g (CH$_3$Cp)$_2$TiF$_2$ | 50 ml | 16.9 g of 1-bromo-2-(trifluoromethyl)benzene (dimetallated at 3,4-positions) | 250 ml ether | −70° C. |
| 8 | 15.2 g Cp$_2$TiF$_2$ | 50 ml | 12.5 g of 1-bromo-2-(trifluoromethyl)-6-fluorobenzene (dimetallated at 3,4-positions) | 200 ml ether 50 ml THF | −70° C. |
| 9 | 8.7 g Cp$_2$TiCl$_2$ | 25 ml | 9.4 g of 1,4-bis(trifluoromethyl)benzene (dimetallated at 2,3-positions) | 100 ml ether 6 ml tetramethyl-ethylenediamine | −70° C. |
| 10 | 9.8 g (CH$_3$Cp)$_2$TiCl$_2$ | 25 ml | 9.4 g of 1,4-bis(trifluoromethyl)benzene (dimetallated at 2,3-positions) | 100 ml ether 6 ml tetramethyl-ethylenediamine | −70° C. |
| 11 | 3.6 g (4,5,6,7-Tetra-hydroindenyl)$_2$TiCl$_2$ | 8.1 ml | 2.7 g of 1-bromo-2-(trifluoromethyl)benzene (dimetallated at 3,4-positions) | 75 ml ether | −70° C. |

| Example | Ti compound | Alkali metal salt | Solvent | Temperature | Reaction time (hours) |
|---|---|---|---|---|---|
| 12 | 9.7 g from Example 3 | 2.75 g KSCN | 125 ml acetone | room temperature | 18 |
| 13 | 9.7 g from Example 3 | 2.75 g KOCN | 125 ml acetone | room temperature | 48 |

TABLE 1-continued

| | | Starting material/reaction conditions | | | |
|---|---|---|---|---|---|
| 14 | 9.7 g from Example 3 | 1.75 g KCN | 125 ml acetone | room temperature | 48 |
| 15 | 9.7 g from Example 3 | 1.75 g NaN₃ | 125 ml acetone | room temperature | 48 |
| 16 | 17.9 g from Example 1 | 5.5 g KSCN | 250 ml acetone | room temperature | 26 |
| 17 | 9.0 g from Example 1 | 2.75 g KOCN | 125 ml acetone | reflux | 2 |
| 18 | 9.0 g from Example 1 | 1.75 g NaN₃ | 125 ml acetone | room temperature | 96 |
| 19 | 9.0 g from Example 1 | 2.26 g NaO(O)CCH₃ | 250 ml tetrahydrofuran | room temperature | 48 |
| 20 | 9.7 g from Example 3 | 3.74 g NaO(O)CCF₃ | 250 ml tetrahydrofuran | room temperature | 48 |

TABLE 2

Products and properties

| Examples | Formula | Yield (%) | Colour | Decomposition point (°C.) | Properties |
|---|---|---|---|---|---|
| 1 | 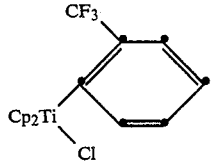 | 88 | orange | 157 | light-sensitive |
| 2 | 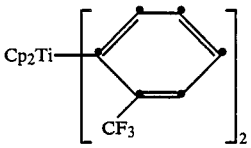 | 49 | yellow | 215 | light-sensitive |
| 3 | 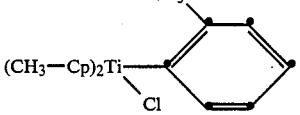 | 94 | orange | 138 | light-sensitive |
| 4 | 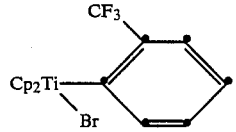 | 70 | orange | 136 | light-sensitive |
| 5 | 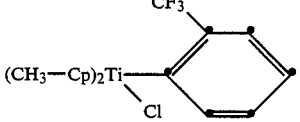 | 79 | orange | 118 | light-sensitive |
| 6 | 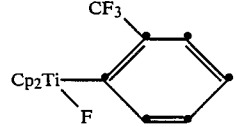 | 93 | yellow | 192 | light-sensitive |
| 7 | 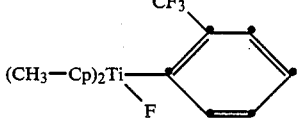 | 30 | yellow | 202 | light-sensitive |
| 8 | 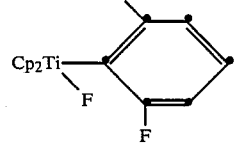 | 25 | orange | 224 | light-sensitive |

TABLE 2-continued

Products and properties

| Examples | Formula | Yield (%) | Colour | Decomposition point (°C.) | Properties |
|---|---|---|---|---|---|
| 9 | Cp$_2$Ti(Cl)—[2-CF$_3$, 5-CF$_3$-C$_6$H$_3$] | 60 | orange | 190 | light-sensitive |
| 10 | (CH$_3$Cp)$_2$Ti(Cl)—[2-CF$_3$, 5-CF$_3$-C$_6$H$_3$] | 85 | orange | 135 | light-sensitive |
| 11 | (4,5,6,7-Tetrahydroindenyl)$_2$Ti(Cl)—[2-CF$_3$, 5-CF$_3$-C$_6$H$_3$] | 50 | orange | 125 | light-sensitive |
| 12 | (CH$_3$—Cp)$_2$Ti(NCS)—[2-CF$_3$-C$_6$H$_4$] | 71 | dark orange | 158 | light-sensitive |
| 13 | (CH$_3$—Cp)$_2$Ti(NCO)—[2-CF$_3$-C$_6$H$_4$] | 100 | orange | 148 | light-sensitive |
| 14 | (CH$_3$—Cp)$_2$Ti(CN)—[2-CF$_3$-C$_6$H$_4$] | 100 | orange | 140 | light-sensitive |
| 15 | (CH$_3$—Cp)$_2$Ti(N$_3$)—[2-CF$_3$-C$_6$H$_4$] | 78 | orange | 158 | light-sensitive |
| 16 | Cp$_2$Ti(NCS)—[2-CF$_3$-C$_6$H$_4$] | 87 | orange | 140 | light-sensitive |
| 17 | Cp$_2$Ti(NCO)—[2-CF$_3$-C$_6$H$_4$] | 73 | orange-yellow | 140 | light-sensitive |
| 18 | Cp$_2$Ti(N$_3$)—[2-CF$_3$-C$_6$H$_4$] | 87 | orange | 160 | light-sensitive |

TABLE 2-continued

| Examples | Formula | Yield (%) | Colour | Decomposition point (°C.) | Properties |
|---|---|---|---|---|---|
| 19 | 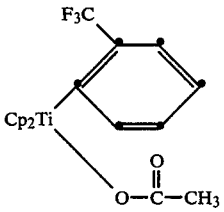 | 80 | orange | 150 | light-sensitive |
| 20 | 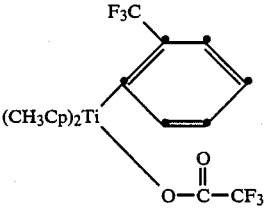 | 90 | orange | 135 | light-sensitive |

APPLICATION EXAMPLES

EXAMPLES 21-40

All the operations are carried out under red light.

A coating solution of the following composition is prepared:
- 6.96 g of 1-acetoxy-2-ethoxyethane
- 1.37 g of a styrene/maleic anhydride copolymer of $\overline{Mw}$ 10,000 (acid number 190)
- 1.47 g of trimethylolpropane triacrylate
- 0.20 g of polyethylene glycol 200 diacrylate
- 0.05 g of initiator The components are mixed and the mixture is stirred until a solution is obtained. Using a wire draw bar, the solution is coated in a wet film thickness of 24 μm onto a pretreated aluminium carrier foil (offset plate substrate) and the coating is dried for 2 minutes at 100° C. A protective polyvinyl alcohol layer consisting of a solution of the following composition is applied to the dry light-sensitive layer:
- 30 g of polyvinyl alcohol (Mowiol 4-88)
- 15 g of polyoxyethylene lauryl ether (Brij 35)
- 250 ml of deionized water A coating of 12 μm wet film thickness is applied and this is dried for 5 minutes at 100° C.

The light-sensitive material is exposed in contact with a test negative which contains a grey wedge with density increments of OD=0.15 (Stauffer wedge). The exposure apparatus used in a photoresist illuminator (Oriel) with a 1 KW Hg/Xe burner (43 mJ/cm² at 365 nm).

The relief image is developed by dipping into a developer solution of the following composition:
- 15.0 g of sodium metasilicate.9H₂O
- 0.3 g of strontium hydroxide.8H₂O
- 3.0 g of polyethylene glycol 6000
- 0.5 g of laevulinic acid
- 1,000.0 g of deionized water at room temperature for 1 minute, briefly rinsed with water and dried in air.

The sensitivity is determined by counting the number of the wedge steps reproduced. The results are shown in Table 3 which follows.

TABLE 3

| Example No. | Initiator from Example No. | Number of wedge steps reproduced after seconds exposure time | | | | |
|---|---|---|---|---|---|---|
| | | 1 | 2 | 4 | 8 | 16 |
| 21 | 1 | 1 | 5 | 7 | 9 | — |
| 22 | 2 | — | — | — | 5 | 7 |
| 23 | 3 | 3 | 5 | 7 | 9 | — |
| 24 | 4 | 4 | — | 6 | 8 | 10 |
| 25 | 5 | 5 | — | 6 | 8 | 10 |
| 26 | 6 | — | — | 4 | 6 | 8 |
| 27 | 7 | — | — | — | 3 | 5 |
| 28 | 8 | — | — | — | 2 | 4 |
| 29 | 9 | — | 3 | 6 | 8 | — |
| 30 | 10 | 2 | 5 | 7 | 10 | — |
| 31 | 11 | — | 4 | 6 | 9 | — |
| 32 | 12 | 4 | 6 | 8 | 10 | — |
| 33 | 13 | 2 | 4 | 6 | 8 | — |
| 34 | 14 | 3 | — | 6 | 8 | 10 |
| 35 | 15 | 3 | 5 | 7 | 9 | — |
| 36 | 16 | 4 | 6 | 8 | 10 | — |
| 37 | 17 | 1 | — | 5 | 7 | 9 |
| 38 | 18 | 1 | — | 5 | 7 | 9 |
| 39 | 19 | 1 | 4 | 5 | 8 | — |
| 40 | 20 | 4 | 6 | 9 | 11 | — |

EXAMPLES 41-50

Composition of the coating solution:
- 6.96 g of 1-acetoxy-2-ethoxyethane
- 1.37 g of styrene/maleic anhydride copolymer of $\overline{Mw}$ 10,000 (acid number 190)
- 1.47 g of trimethylolpropane triacrylate
- 0.20 g of polyethylene glycol 200 diacrylate
- 0.05 g of initiator
- 0.05 g of sensitizer The procedure followed is analogous to Example 21. The results are shown in Table 4.

TABLE 4

| Example No. | Initiator from Example No. | Sensitizer | Number of wedge steps reproduced after seconds exposure time | | | |
|---|---|---|---|---|---|---|
| | | | 0.5 | 1 | 2 | 4 |
| 41 | 3 | *(thioxanthone with H3C and COOC2H5 substituents)* | 6 | 7 | 9 | — |
| 42 | 7 | | — | 5 | 7 | 9 |
| 43 | 17 | | 7 | 7 | 9 | — |
| 44 | 12 | *(thioxanthone derivative with N,C—CH2—C(CH3)3 substituent)* | — | 6 | 8 | 9 |
| 45 | 5 | | — | 7 | 8 | 10 |
| 46 | 5 | *(thioxanthone with two isopropyl groups)* | 3 | 9 | — | — |
| 47 | 6 | | — | 6 | 8 | 10 |
| 48 | 8 | | — | 4 | 5 | 8 |
| 49 | 20 | | 7 | 9 | 11 | — |
| 50 | 5 | *(4,4′-bis(dimethylamino)benzophenone)* | — | 10 | — | — |

What is claimed is:

1. A titanocene of the formula I $$\begin{array}{c} R^1 \\ \phantom{R^1}\diagdown \\ \phantom{R^1}\phantom{\diagdown}Ti \\ \phantom{R^1}\diagup\phantom{Ti}\diagdown \\ R^1 \phantom{\diagup Ti\diagdown} R^3 \end{array} \begin{array}{c} R^2 \\ \end{array}$$  (I)

in which the two $R^1$ independently of one another are cyclopentadienyl$^\ominus$, indenyl$^\ominus$ or 4,5,6,7-tetrahydroindenyl$^\ominus$, or both $R^1$ together are an unsubstituted or substituted radical of the formula II

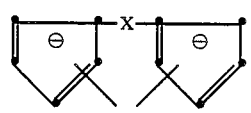  (II)

in which X is —(CH$_2$)$_n$ with n=1, 2 or 3 alkylidene having 2 to 12 C atoms, cycloalkylidene having 5 to 7 ring carbon atoms, SiR$_2^4$ or SnR$_2^4$, and $R^4$ is $C_1$–$C_{12}$-alkyl, $C_5$–$C_{12}$-cycloalkyl, $C_6$–$C_{16}$-aryl or $C_7$–$C_{16}$-aralkyl, or $R^1$ is said cyclopentadienyl, indenyl, 4,5,6,7-tetrahydroindenyl or radical of formula II which is substituted by alkyl, by alkoxy or by alkenyl of up to 18 carbon atoms, by cycloalkyl or by cycloalkenyl of 5 to 8 ring carbon atoms; by aryl of 6 to 16 carbon atoms; by aralkyl of 7 L to 16 carbon atoms; by halogen; by amino or by aminoalkyl of up to 12 carbon atoms wherein the amino groups are unsubstituted or substituted by alkyl of up to 12 carbon atoms or quaternized with an alkyl halide of up to 12 carbon atoms, $R^2$ is a 6-membered carboxyclic or 5-membered or 6-membered heterocyclic aromatic ring which is substituted in at least one of the two ortho-positions relative to the metal-carbon bond by —CF$_2$Z, in which Z is F or unsubstituted or substituted alkyl, or wherein said aromatic ring of $R^2$ is further substituted by alkyl or by alkoxy of 1 to 18 carbon atoms; by cycloalkyl of 5 to 6 ring carbon atoms; by aryl of 6 to 16 carbon atoms; by aralkyl of 7 to 16 carbon atoms; by hydroxyl; by carboxyl; by halogen; by cyano; by amino which is unsubstituted or substituted by alkyl or quaternized by an alkyl halide; by pyrrolidino, by piperidino, by piperazino, by morpholino or by N-methylpiperazino; by alkoxycarbonyl of 1 to 18 carbon atoms, in the alkoxy moiety; by aminocarbonyl containing one or two $C_1$-$C_{12}$alkyl groups in the amonio moiety; or by aminocarbonyl containing a pyrrolidino, piperidino, piperazino, N-methylpiperazino or morpholino group; or by aminoalkyl of up to 6 carbon atoms wherein the amino group is unsubstituted or substituted by alkyl of up to 12 carbon atoms or quaternized with an alkyl halide of up to 12 carbon atoms and $R^3$ is as defined for $R^2$ or is halogen, cyanate, thiocyanate, azide, cyano, —OH, alkoxy, alkylthio, aryloxy, arylthio, acyloxy, a group of the formula $R^{10}R^{11}N$— in which $R^{10}$ and $R^{11}$ are $C_1$-$C_{12}$alkyl, unsubstituted or alkyl substituted cyclopentyl, cyclohexyl, phenyl or benzyl, or $R^{10}$ and $R^{11}$ together are tetra-, penta- or hexamethylene which are unsubstituted or alkyl substituted or are interruped by —S—, —O— or

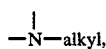

alkynyl, phenylalkynyl, a group of the formula

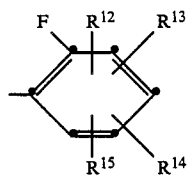

in which $R^{12}$ to $R^{15}$ are hydrogen, fluorine, chlorine, bromine, $C_1$-$C_4$alkyl, dialkylamino having 2 to 12 carbon atoms, trialkylaminomethyl having 3 to 18 carbon atoms or said amino groups being quaternized with $C_1$-$C_6$alkyl halides, $SiR_3$ or $S_nR_3$ $R^4$ being as defined above.

2. A titanocene according to claim 1, wherein $R^1$ is cyclopentadienyl$^\ominus$ or methylcyclopentadienyl$^\ominus$.

3. A titanocene according to claim 1, wherein $R^2$ is a radical of the formula III

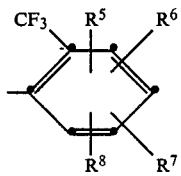

in which $R^5$, $R^6$, $R^7$ and $R^8$ are hydrogen atoms, bromine, chlorine or fluorine.

4. A titanocene according to claim 3, wherein $R^5$, $R^6$ and $R^7$ are hydrogen atoms, and $R^8$ is bonded in the ortho-position relative to the free bond and is fluorine or a hydrogen atom.

5. A titanocene according to claim 1, wherein $R^3$ in the formula I is as defined for $R^2$ or is halogen, cyanate, thiocyanate azide cyano.

6. A titanocene according to claim 1, wherein $R^1$ in the formula I is cyclopentadienyl$^\ominus$ or methylcyclopentadienyl$^\ominus$, $R^2$ is

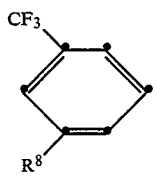

7. A titanocene according to claim 6, wherein $R^3$ is F, Cl, Br, $N_3$, CN, NCO or NCS.

8. The compound of formula I according to claim 1 wherein each of $R^1$ is cyclopentadienyl, $R^2$ is o-trifluoromethylphenyl, and $R^3$ is chloro.

* * * * *